US009757310B2

(12) United States Patent
Jahns

(10) Patent No.: US 9,757,310 B2
(45) Date of Patent: Sep. 12, 2017

(54) FLUORESCENCE IMPARTING COLORING SOLUTION FOR DENTAL CERAMICS

(71) Applicant: 3M INNOVATIVE PROPERTIES COMPANY, St. Paul, MN (US)

(72) Inventor: Michael Jahns, Gilching (DE)

( * ) Notice: Subject to any disclaimer, the term of this patent is extended or adjusted under 35 U.S.C. 154(b) by 48 days.

(21) Appl. No.: 14/774,485

(22) PCT Filed: Mar. 6, 2014

(86) PCT No.: PCT/US2014/021185
§ 371 (c)(1),
(2) Date: Sep. 10, 2015

(87) PCT Pub. No.: WO2014/164199
PCT Pub. Date: Oct. 9, 2014

(65) Prior Publication Data
US 2016/0038381 A1 Feb. 11, 2016

(30) Foreign Application Priority Data

Mar. 12, 2013 (EP) ..................... 13158790

(51) Int. Cl.
| A61K 6/00 | (2006.01) |
| C04B 41/81 | (2006.01) |
| C04B 41/00 | (2006.01) |
| C04B 41/45 | (2006.01) |
| C04B 41/85 | (2006.01) |
| A61K 6/02 | (2006.01) |
| C04B 111/00 | (2006.01) |
| C04B 111/80 | (2006.01) |

(52) U.S. Cl.
CPC .......... *A61K 6/0094* (2013.01); *A61K 6/0002* (2013.01); *A61K 6/024* (2013.01); *A61K 6/025* (2013.01); *A61K 6/0255* (2013.01); *C04B 41/009* (2013.01); *C04B 41/4535* (2013.01); *C04B 41/81* (2013.01); *C04B 41/85* (2013.01); *C04B 2111/00836* (2013.01); *C04B 2111/807* (2013.01)

(58) Field of Classification Search
CPC ........................... A61K 6/0094; A61K 6/0002
USPC ........................................... 427/2.29; 106/35
See application file for complete search history.

(56) References Cited

U.S. PATENT DOCUMENTS

| 2,807,555 | A | 9/1957 | Short |
| 3,027,331 | A | 3/1962 | Nils |
| 3,141,780 | A | 7/1964 | Simon |
| 3,350,922 | A | 11/1967 | Kim |
| 3,520,659 | A | 7/1970 | Steinberg |
| 3,741,441 | A | 6/1973 | Eberle |
| 3,802,605 | A | 4/1974 | Standlickl |
| 4,168,018 | A | 9/1979 | Zahaykevich |
| 4,189,325 | A | 2/1980 | Barrett et al. |
| 4,472,963 | A | 9/1984 | Gyer |
| 4,546,006 | A | 10/1985 | Ohno et al. |
| 4,550,030 | A | 10/1985 | Ohi et al. |
| 4,612,800 | A | 9/1986 | Erian |
| 4,681,633 | A | 7/1987 | Watanabe et al. |
| 4,772,436 | A | 9/1988 | Tyszblat |
| 4,828,117 | A | 5/1989 | Panzera et al. |
| 5,011,403 | A | 4/1991 | Sadoun et al. |
| 5,017,790 | A | 5/1991 | Kojima |
| 5,063,255 | A | 11/1991 | Hasegawa |
| 5,091,033 | A | 2/1992 | Nakabayaski et al. |
| 5,106,303 | A | 4/1992 | Oden et al. |
| 5,145,250 | A | 9/1992 | Planck |
| 5,219,805 | A | 6/1993 | Yoshida et al. |
| 5,233,916 | A | 8/1993 | Butler |
| 5,249,862 | A | 10/1993 | Herold |
| 5,250,352 | A | 10/1993 | Tyszblat |
| 5,263,858 | A | 11/1993 | Yoshida et al. |
| 5,286,105 | A | 2/1994 | Herold |
| 5,447,967 | A | 9/1995 | Tyszblat |
| 5,499,745 | A | 3/1996 | Derian |
| 5,565,152 | A | 10/1996 | Oden et al. |
| 5,618,585 | A | 4/1997 | Hechler et al. |
| 5,799,832 | A | 9/1998 | Mayo |
| 5,821,407 | A | 10/1998 | Sekiguchi |
| 5,854,076 | A | 12/1998 | Kundu |
| 5,869,548 | A | 2/1999 | Ikushima et al. |
| 6,010,337 | A | 1/2000 | Billet |
| 6,042,884 | A | 3/2000 | Klein et al. |
| 6,058,721 | A | 5/2000 | Midden |

(Continued)

FOREIGN PATENT DOCUMENTS

| DE | 2012304 | 9/1971 |
| DE | 3109927 | 9/1982 |

(Continued)

OTHER PUBLICATIONS

Shah et al. Effects of coloring with various metal oxides on the microstructure, color, and flexural strength of 3Y-TZP. Journal of BIomaterials Research. vol. 87B Issue 2 Nov. 2008 pp. 329-337.*
Rieger, Aluminum and Zirconium Oxide Ceramics in Medicine: Industrie Diamanten Rundschau, IDR 2, 1993, pp. 1-7.
Cales, Colored Zirconia Ceramics for Dental Applications, Bioceramics, vol. 11, 1998, 3 sheets.
Todorosxky et al., "Preparation and Charactgerization of Yttrium-iron Citric Acid Complexes" *Croatica Chemica Acta*, vol. 75, No. 1, 2002, pp. 155-164, XP002440842.
Written Opinion of the ISA for International Application No. PCT/US2008/053393, pp. 5.
Search Report for PCT/US2008/053393.
Ext. European Search Report for EP 07002726.

(Continued)

*Primary Examiner* — Cachet Sellman

(57) ABSTRACT

The invention relates to a solution for coloring and imparting fluorescence to a zirconia dental article, the solution comprising: •a solvent, •a coloring agent comprising ions selected from Tb, Er, Pr, Mn and combinations thereof, •a fluorescing agent comprising ions of Bi, the solution not comprising Fe ions in an amount above about 0.05 wt.-% with respect to the weight of the whole solution.

15 Claims, No Drawings

(56) References Cited

U.S. PATENT DOCUMENTS

| | | |
|---|---|---|
| 6,114,054 A | 9/2000 | Klein et al. |
| 6,121,362 A | 9/2000 | Wanek |
| 6,129,450 A | 10/2000 | Braun |
| 6,132,672 A | 10/2000 | Vignali |
| 6,145,373 A | 11/2000 | Tymchuck |
| 6,312,668 B2 | 11/2001 | Mitra |
| 6,464,765 B1 | 10/2002 | Garcia |
| 6,500,001 B2 | 12/2002 | Hörth |
| 6,702,987 B1 | 3/2004 | Kundu |
| 6,709,694 B1 | 3/2004 | Suttor |
| 6,756,421 B1 | 6/2004 | Todo |
| 6,786,994 B2 | 9/2004 | Williams |
| 6,854,349 B2 | 2/2005 | Brandhorst |
| 7,432,037 B2 | 10/2008 | Suzuki et al. |
| 7,669,571 B2 | 3/2010 | Delgado |
| 8,119,058 B2 | 2/2012 | Franke |
| 8,685,278 B2 | 4/2014 | Yamada |
| 9,439,838 B2 | 9/2016 | Jahns |
| 2006/0117989 A1 | 6/2006 | Hauptmann |
| 2007/0062410 A1 | 3/2007 | Thiel |
| 2010/0047438 A1 | 2/2010 | Hauptmann |
| 2010/0062398 A1 | 3/2010 | Schechner |
| 2010/0221683 A1 | 9/2010 | Franke |
| 2012/0012789 A1 | 1/2012 | Yamada |
| 2013/0341812 A1 | 12/2013 | Schechner |
| 2014/0252272 A1 | 9/2014 | Durschang |
| 2014/0367613 A1* | 12/2014 | Mashio ............. C04B 35/486 252/301.36 |

FOREIGN PATENT DOCUMENTS

| | | | |
|---|---|---|---|
| DE | 4320072 | 5/1994 | |
| DE | 19619165 | 9/1997 | |
| DE | 19619168 | 10/1997 | |
| DE | WO 2012125885 A1 * | 9/2012 | ........... A61K 6/0094 |
| DE | WO 2013022612 A1 * | 2/2013 | ............... A61K 6/06 |
| EP | 0230534 | 5/1987 | |
| EP | 0816305 A1 | 1/1998 | |
| GB | 421872 | 1/1935 | |
| JP | 214866 | 6/1988 | |
| JP | 3-5366 A | 1/1991 | |
| JP | 3-170148 A | 7/1991 | |
| JP | 3-198841 | 8/1991 | |
| JP | 05-043361 | 5/1993 | |
| JP | 06-345566 | 12/1994 | |
| JP | 8-33650 A | 2/1996 | |
| JP | 08-337484 | 12/1996 | |
| JP | 9-110563 | 4/1997 | |
| JP | 9-142966 | 6/1997 | |
| JP | 2004-149587 | 5/2004 | |
| JP | 2005-281414 | 10/2005 | |
| JP | 2005-298596 | 10/2005 | |
| JP | 2006002100 | 1/2006 | |
| JP | 2006-176762 | 7/2006 | |
| JP | 2007-015946 | 1/2007 | |
| JP | 2007-031288 | 2/2007 | |
| JP | 2007-039475 | 2/2007 | |
| JP | 2007-131841 | 5/2007 | |
| WO | WO 83/02712 | 8/1983 | |
| WO | WO 9843727 | 10/1998 | |
| WO | WO 2012/175615 | 12/2012 | |

OTHER PUBLICATIONS

Search Report for PCT/EP00/00910.
Written Opinion from PCT/EP2004/006220.
Nakumura, T. et al., "Clinical Applications of a Newly Developed Hybrid Ceramic Composite for Posterior Prostheses," Quintessence of Dental Technology (1999), pp. 83-93.
"Masters in Concert: Interview" Dr. Gerard Chiche and Mr. Hitoshi Aoshima, Quintessence of Dental Technology, vol. 20 (1997), p. 10-20.
Mutobe, Y. et al., "In Harmony with Nature: Esthetic Restoration of a Nonvital Tooth with IPS-Empress All-Ceramic Material," Quintessence of Dental Technology, vol. 20 (1997), pp. 83-106.
"VITA-HI-Ceram Working Instructions" (pub'd Aug. 1990).
"The Vitadur Technique, Working Instructions," 5th ed. (pub'd Sep. 1990).
Naylor, W., "Introduction to Metal Ceramic Technology" (1992), pp. 138-139.
McLean, J., "The Science and Art of Dental Ceramics," Monographs III and IV (2nd printing, 1978) pp. 7, 26.
Aoshima, H., "Aesthetic All-Ceramic Restorations: The Internal Live Stain Technique," PP&A, vol. 9, No. 8 (1997) pp. 861-868.
Craig, R., "Restorative Dental Materials," 7th Edition, Chapter 17, pp. 432-449.
McLean, "The Science and Art of Dental Ceramics", vol. 1, 1979, pp. 7, 26.
McLean, "The Science and Art of Dental Ceramics", vol. 2, 1980, pp. 7, 26.
Yamamoto, M., "Metal Ceramics: Principles and Methods of Makoto Yamamoto", 1985.
Sorensen, J. et al., "In-Ceram Fixed Partial Dentures: Three-Year Clinical Trial Results," Journal of the California Dental Association, vol. 26, No. 3 (Mar. 1998) pp. 207-214.
Fulmer, J. et al., "Tensile, Impact and Fatigue Performance of a New Water Atomized Low-Alloy Powder— Ancorsteel 85 HP," (1990) pp. 1, 4.
Ocana, M. et al., "Preparation by Hydrolysis of Aerosols and Colour Properties for Cr-Doped and Co-Doped Zircon Powders," Journal of the European Ceramic Society 18 (1998) pp. 821-830.
"Ceramic Products Manufacturing," (1996) 11.7-1-11.7-13.
Industrie Diamanten Rundschau IDR Feb. 1993 "Aluminum und Zirkonoxidkeramik in der Medizin".
Pamphlet relating to the Cerec System—"Okonomie durch Technologie".
Pamphlet relating to the Procera system.
Hawley's Chemical Dictionary, 13th Ed., pp. 852-853.
Table of Periodic Properties of the Elements, Sargent-Welch Scientific Company, Illinois 1980.
Shah, K., "Effect of Coloring wit hCarious Metal Oxides on the Microstructur4e, Color, and Flecural Strength of 3Y-TZP," Feb. 12, 2007, pp. 329-337.

* cited by examiner

FLUORESCENCE IMPARTING COLORING SOLUTION FOR DENTAL CERAMICS

FIELD OF THE INVENTION

The invention relates to a coloring solution for coloring dental ceramic materials. The coloring solutions contains coloring agent(s) and fluorescing agent(s).

BACKGROUND ART

Commercially available coloring solutions typically comprise water, metal cations selected from rare earth elements, transition metal and mixtures thereof, optionally complexing agent(s) and/or further additives like (poly)ethylene glycol. The coloring solutions are typically used for homogeneously coloring of porous dental ceramics. The coloring solutions are applied to the dental ceramic being in a porous and absorbent stage. After sintering, the dental ceramic usually shows a tooth-like color and is ready for veneering.

WO 2004/110959 (3M) relates to a coloring solution for ceramic framework. The solution comprises a solvent (e.g. water), a metal salt and polyethylene glycol having a Mn in the range of 1,000 to 200,000.

WO 00/46168 A1 (3M), corresponding to U.S. Pat. No. 6,709,694 B1 refers to coloring ceramics by way of ionic or complex-containing solutions containing defined concentrations of at least one salts or complexes of the rare earth elements or of the elements of the subgroups. The solution might contain additives like stabilizers, complex builders, pigments and beating additives.

WO 2008/098157 (3M) relates to a coloring solution for dental ceramic framework comprising a solvent, a coloring agent comprising metal ions, and a complexing agent, wherein the amount of complexing agent is sufficient to dissolve the coloring agent in the solvent.

WO 2009/014903 (3M) relates to a coloring solution for dental ceramic articles, the solution comprising a solvent and a coloring agent comprising rare earth element ions being present in the solution in an amount of at least about 0.05 mol/l solvent and transition ions being present in the solution in an amount of about 0.00001 to about 0.05 mol/l solvent.

WO 2010/062541 (3M) relates to a dental ceramic article comprising zirconium oxide and at least two different coloring substances showing light emission in the range of about 470 nm to 510 nm and light absorption in the range from about 520 nm to about 750 nm.

WO 2011/146761 (3M) relates to a dental article comprising two sections A and B, section A comprising zirconia in a certain amount and Dy, Sm, Eu or a mixture thereof, section B comprising a glass, glass ceramic or composite material.

WO 2013/022612 (3M) describes coloring solutions for selectively treating the surface of dental ceramic and related methods. The solution may comprise a solvent being miscible with water but not being water, an effect agent comprising metal ions, the effect caused by the effect agent being either coloring, providing fluorescence or a combination thereof, and a complexing agent being able to form a complex with the metal ions of the effect agent, wherein the complex is soluble in the solvent.

WO 2012/125885 (3M) relates to a dental ceramic article, process of production and use thereof. The dental ceramic article comprises ceramic components, the ceramic components comprising ZrO2 and Al2O3 and at least one component comprising Mn, Er or mixtures thereof. Described is also a kit of parts comprising a ceramic article and a coloring solution and process for producing a dental ceramic article. The content of these references is herewith incorporated by reference.

However, there is still room for improvement especially with regard to the requirements to be fulfilled with respect to modern dental materials. Patients and dentists nowadays have an increasing demand for highly aesthetic dental restorations.

DESCRIPTION OF THE INVENTION

The complex structure of a natural tooth leads to a demand for a means enabling the practitioner to provide a dental ceramic with the potential to be individual colorable without sacrificing the brightness. If possible, this means should be easy to apply and comparable cheap in production. In particular, there is a need to mimic the natural tooth appearance in dental restorations taking into account individual degrees of color and brightness of the hard dental tissue e.g. of enamel and dentin.

Alternatively or in addition it should be possible to produce a dental restoration out of a monolithic block in an economic way if possible without significant loss of strength and durability.

In one aspect the invention is directed to a solution for coloring and imparting fluorescence to a zirconia dental article, the solution comprising:
  a solvent,
  a coloring agent comprising ions selected from Tb, Er, Pr, Mn and combinations thereof,
  a fluorescing agent comprising ions of Bi,
  the solution not comprising Fe ions in an amount above about 0.05 wt.-% with respect to the weight of the whole solution.

The invention is also related to a kit of parts comprising:
  a solution as described in the present text, the solution being optionally be contained in a device as described in the present text,
  a zirconia dental article,
  optionally application equipment, and
  optionally an instruction for use.

Moreover, the invention features a process of coloring a zirconia dental article, the process comprising the steps of:
  providing a zirconia dental article, the zirconia dental article being porous,
  treating the zirconia dental article with the solution,
  optionally heating the treated porous zirconia dental article until at least about 90 or at least about 95 or at least about 99% of the theoretical density is achieved.

Definitions

A "solution" shall mean a composition containing solvent with soluble components dissolved therein. The solution is a liquid at ambient conditions.

A "solvent" is any solvent which is able to dissolve the colouring agent. The solvent should be sufficiently chemically stable if combined with the coloring agent. That is, the solvent shall not be decomposed by the other components present in the composition.

"Soluble" means that a component (solid) can be completely dissolved within a solvent. That is, the substance is able to form individual molecules (like glucose) or ions (like sodium cations or chloride anions) when dispersed in water at 23° C. The solution process, however, might take some time, e.g. stirring the composition over a couple of hours (e.g. 10 or 20 h) might be required.

A solution can be classified as "storage stable", if it remains stable over a considerable long period of time (at least about 4 weeks to more than about 12 months under ambient conditions). A storage stable solution typically does not show any visible (visible to the human eye) precipitation of the coloring agent during storage at ambient conditions (about 23° C., about 1013 mbar) and does not show decomposition of the solution or precipitation of single or multiple components.

"Coloring ions" shall mean ions which have an absorption in the spectrum visible to the human eye (e.g. from about 380 to about 780 nm), which results in a colored solution (visible to the human eye), if the coloring ions are dissolved in water (e.g. about 0.6 mol/l) and/or cause a coloring effect in the zirconia article which has been treated with the coloring solution and sintered afterwards.

A solution can be characterized as "transparent" within the meaning of the invention if a beam of visible light (about 380 to about 780 nm) is not scattered by the solution and cannot be observed by side view (i.e. no Tyndall effect). However, the intensity of the penetrating beam of visible light in direction of the beam may be weakened due to absorption of the light by the coloring ions.

A solution is defined as "non-colored", if the a* and b* values (of the L*a*b* CIELAB color space) are as follows: a* being within a range of 0±5 or 0±3; b* being within a range of 0±20 or 0±10.

A solution is defined as "colored", if the a* and b* values (of the L*a*b* CIELAB color space) are as follows: a* being within a range of above about 5, b* being within a range of above about 20.

The three coordinates of CIELAB represent the lightness of the color (L*=0 yields black and L*=100 indicates diffuse white; specular white may be higher), its position between red/magenta and green (a*, negative values indicate green while positive values indicate magenta) and its position between yellow and blue (b*, negative values indicate blue and positive values indicate yellow).

A composition is "essentially or substantially free of" a certain component, if the composition does not contain said component as an essential feature. Thus, said component is not willfully added to the composition either as such or in combination with other components or ingredient of other components. A composition being essentially free of a certain component usually contains the component in an amount of less than about 1 wt.-% or less than about 0.5 wt.-% or less than about 0.1 wt.-% or less than about 0.01 wt.-% with respect to the whole composition or material. The composition may not contain the said component at all. However, sometimes the presence of a small amount of the said component is not avoidable e.g. due to impurities contained in the raw materials used.

"Zirconia article" shall mean a 3-dimensional article wherein at least one the x, y, z dimension is at least about 5 mm, the article being comprised of at least about 80 or at least about 90 or at least about 95 wt.-% zirconia.

"Ceramic" means an inorganic non-metallic material that is produced by application of heat. Ceramics are usually hard, porous and brittle and, in contrast to glasses or glass ceramics, display an essentially purely crystalline structure.

"Crystalline" means a solid composed of atoms arranged in a pattern periodic in three dimensions (i.e., has long range crystal structure as determined by X-ray diffraction). Crystal structures include tetragonal, monoclinic, cubic zirconia and mixtures thereof.

The term "dental article" means any article which is to be used in the dental or orthodontic field, especially for producing of or as dental restoration, a tooth model and parts thereof. Examples of dental articles include crowns (including monolithic crowns), bridges, inlays, onlays, veneers, facings, copings, crown and bridged framework, implants, abutments, orthodontic appliances (e.g. brackets, buccal tubes, cleats and buttons), dental mill blocks and parts thereof. The surface of a tooth is considered not to be a dental article.

A dental article should not contain components which are detrimental to the patient's health and thus free of hazardous and toxic components being able to migrate out of the dental article.

"Monolithic dental restoration" shall mean a dental ceramic article onto the surface of which no facing or veneer has been attached. That is, the monolithic dental restoration is essentially comprised out of only one material composition. However, if desired a thin glazing layer can be applied.

"Density" means the ratio of mass to volume of an object. The unit of density is typically $g/cm^3$. The density of an object can be calculated e.g. by determining its volume (e.g. by calculation or applying the Archimedes principle or method) and measuring its mass.

The volume of a sample can be determined based on the overall outer dimensions of the sample. The density of the sample can be calculated from the measured sample volume and the sample mass. The total volume of the ceramic material can be calculated from the mass of the sample and the density of the used material. The total volume of cells in the sample is assumed to be the remainder of the sample volume (100% minus the total volume of material).

An article is classified as "absorbent" if the article is able to absorb a certain amount of a liquid, comparable to a sponge. The amount of liquid which can be absorbed depends e.g. on the chemical nature of the article, the viscosity of the solvent, the porosity and pore volume of the article. E.g. a pre-sintered ceramic article, that is an article which has not been sintered to full density, is able to absorb a certain amount of liquid. Absorbing of liquids is typically only possible if the article has an open-porous structure.

A "porous material" refers to a material comprising a partial volume that is formed by voids, pores, or cells in the technical field of ceramics. Accordingly an "open-celled" structure of a material sometimes is referred to as "open-porous" structure, and a "closed-celled" material structure sometimes is referred to as a "closed-porous" structure. It may also be found that instead of the term "cell" sometimes "pore" is used in this technical field. The material structure categories "open-celled" and "closed-celled" can be determined for different porosities measured at different material samples (e.g. using a mercury "Poremaster 60-GT" from Quantachrome Inc., USA) according to DIN 66133. A material having an open-celled or open-porous structure can be passed through by e.g. gases.

Typical values for an "open-celled" material are between about 15% and about 75% or between about 18% and about 75%, or between about 30% and about 70%, or between about 34% and about 67%, or between about 40% to about 68%, or between about 42% and about 67%.

The term "closed-celled" relates to a "closed porosity". Closed cells are those cells which are not accessible from the outside and cannot be infiltrated by gases under ambient conditions.

The "average connected pore diameter" means the average size of the open-celled pores of a material. The average connected pore diameter can be calculated as described in the Examples section.

The terms "sintering" or "firing" are used interchangeably. A pre-sintered ceramic article shrinks during a sintering step, that is, if an adequate temperature is applied. The sintering temperature to be applied depends on the ceramic material chosen. For $ZrO_2$ based ceramics a typical sintering temperature range is about 1100° C. to about 1550° C. Sintering typically includes the densification of a porous material to a less porous material (or a material having less cells) having a higher density, in some cases sintering may also include changes of the material phase composition (for example, a partial conversion of an amorphous phase toward a crystalline phase).

The term "aerogel" shall mean a three-dimensional low density (i.e., less than 20% of theoretical density) solid. An aerogel is a porous material derived from a gel, in which the liquid component of the gel has been replaced with a gas. The solvent removal is often done under supercritical conditions. During this process the network does not substantially shrink and a highly porous, low-density material can be obtained.

By "machining" is meant milling, grinding, cutting, carving, or shaping a material by a machine. Milling is usually faster and more cost effective than grinding. A "machinable article" is an article having a 3-dimensional shape and having sufficient strength to be machined.

"Ambient conditions" mean the conditions which the inventive solution is usually subjected to during storage and handling. Ambient conditions may, for example, be a pressure of about 900 to about 1100 mbar, a temperature of about 10 to about 40° C. and a relative humidity of about 10 to about 100%. In the laboratory ambient conditions are adjusted to about 20 to about 25° C. and about 1000 to about 1025 mbar.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.). The term "comprise" shall include also the terms "consist essentially of" and "consists of".

A "fluorescing agent" shall mean an agent showing fluorescence in the region of visible light (about 380 to about 780 nm).

A "complexing agent" shall mean an agent which is able to form complexes with metal ions contained in the coloring solution.

It was found that bismuth is a good additive for adding or imparting fluorescence to a zirconia dental article. Without wishing to be bound to a particular theory, it is believed that this might be caused by bismuth doped zirconia being able to emit a high portion of light in the region of blue light.

However, using iron as a coloring agent in combination with bismuth was found to be detrimental for the desired fluorescing property. Without wishing to be bound to a particular theory, it is believed that this might be caused by the broad absorption bands of iron in the region of blue light, even if present at low concentrations. Thus, iron may eliminate almost all fluorescence provided or imparted by the use of bismuth.

Iron ions, however, are known as a suitable means for achieving the desired tooth color of the zirconia dental article.

It was found that by using the solution described in the present text, the combined effect of imparting fluorescence and color to a zirconia dental article can be achieved even with a solution not containing iron ions or only containing traces of iron ions.

This effect is typically not limited to bright colors (e.g. A1, B1 or C1 (according to the Vita Classical tooth color scheme) but can be extended to darker colors including A2, B2, C2 and darker. The solution described in the present text is applied to a zirconia article.

According to one embodiment the zirconia article is in a pre-sintered stage or in a stage which allows the ceramic article to be machined. Thus, the ceramic article should have a sufficient raw breaking resistance. This stage is sometimes also called "green body". That is, the material may have already been slightly fired to a certain temperature to increase the raw breaking resistance of the material.

If desired, pre-sintering can be carried out in a temperature range from about 700° C. to about 1100° C. or from about 800° C. to about 1000° C. The ceramic article can be produced by any standard procedure known to the person skilled in the art, including uniaxial pressing, cold isostatic pressing (CIP), rapid-prototyping and slip casting.

If the ceramic article is in a pre-sintered stage (i.e. before having conducted a final sintering or firing step), it can typically be characterized by at least one, more or all of the following features:
  raw breaking resistance: from about 5 to about 55 MPa, or from about 5 to about 30 MPa,
  density: from about 2.4 to about 3.7 g/cm$^3$, or from about 2.5 to about 3.6 g/cm$^3$,
  porosity: from about 40 to about 60 vol.-%.

The pore diameter is typically in a range from about 10 nm to about 500 nm or from about 50 to about 200 nm. According to one embodiment, the average pore diameter is usually in a range of about 100 nm.

If the ceramic article has been sintered to its final stage, it typically fulfils at least one, two or all of the following physical parameters:
  breaking resistance: at least about 400 MPa, or at least about 700 MPa or at least about 1000 MPa,
  density: from about 5.9 to about 6.1 g/cm$^3$ or from about 6.0 to about 6.1 g/cm$^3$, and/or
  light emission, in particular, fluorescence emission with bands in the region of the visible light (e.g. from about 380 nm to about 780 nm).

If desired, the breaking resistance of the sintered dental ceramic article can be determined according to the "punch on three ball test" (biaxial flexural strength) described in DIN EN ISO 6872, edition March 1999, with the following modifications: diameter of steel ball: 3 mm; diameter of support circle: 12 mm; diameter of flat punch: 3.6 mm; diameter of sample disc: 16 mm, thickness of sample disc: 1.6 mm (+/−0.05 mm); grinding of samples with 10 μm disc to be +/−0.05 mm plan parallel and polishing of samples consecutively with 9 and 3 μm.

The density can be obtained from determining the mass (by weighing) and the volume (e.g. by calculation or using the "Archimedes Method"). The material, the zirconia article is made of, can be of different kind. According to one embodiment, the porous zirconia dental article to which the solution is applied has the following composition:

comprising ceramic components, the ceramic components comprising ZrO2 and Al2O3, with Al2O3 being present in an amount of about 0.001 wt.-% to about 0.15 wt.-% with respect to the weight of the ceramic components.

Thus, according to this embodiment, the zirconia material contains only traces of Al2O3. Al2O3 is typically present in an amount below about 0.15 wt.-% or below about 0.14 wt.-% or below about 0.13 wt.-% or below about 0.12 wt.-% or below about 0.11 wt.-% or below about 0.1 wt.-%, wt.-% with respect to the weight of the ceramic components.

Typical ranges for Al2O3 include from 0.0001 to about 0.15 wt.-% or from about 0.001 to about 0.14 wt.-% or from about 0.01 to about 0.13 wt.-% or from about 0.1 to about 0.10 wt.-%. If the content of alumina is outside the above range, in particular present in an amount above about 0.15 wt.-%, it can be difficult to achieve the desired aesthetic properties.

According to one embodiment, the zirconia material may be characterized by the following features (in the sintered ceramic, all components are present as oxides):
ZrO2: from about 80 wt.-% to about 98 wt.-% or from about 85 wt.-% to about 97 wt.-%,
HfO2: from about 0.0001 to about 3 wt.-% with respect to the weight of the article,
Al2O3: from 0.0001 to about 0.15 or from about 0.0001 to about 0.14 wt.-% or from about 0.001 to about 0.12 wt.-%.

As the chemical and physical properties of ZrO2 and HfO2 are pretty similar, a distinction and especially chemical separation between both oxides is not easy. Thus, the amounts of ZrO2 and HfO2 can also be given as ZrO2+HfO2 from about 80 wt.-% to about 98 wt.-% or from about 85 wt.-% to about 97 wt.-%.

Another kind of zirconia material the colouring solution described in the present text can be used with is a zirconia material showing a N2 adsorption and/or desorption of isotherm type IV (according to IUPAC classification) and/or a hysteresis loop (especially in a p/p0 range of 0.70 to 0.95).

Commercially available Y-TZP ceramic materials typically show a N2 adsorption and/or desorption of isotherm type II (according IUPAC classification). Materials showing a type II isotherm are said to be macro-porous, whereas materials showing a type IV isotherm are said to be meso-porous.

In contrast to the porous zirconia article showing a type IV isotherm, zirconia materials described in the prior art do neither show a N2 adsorption and desorption behaviour with a hysteresis loop nor a N2 adsorption and/or desorption of isotherm type IV (according to IUPAC classification).

Without wishing to be bound to a particular theory it is assumed that the condensation mode related to a material of isotherm type IV and a hysteresis loop type H1 may contribute to a more homogeneous infiltration of the solution into the pores of the material.

The coloring solution described in the present text is especially suitable for producing highly aesthetic dental ceramic articles, in particular dental ceramic articles like crowns where different portions of the outer surface of the dental article has been treated with the coloring solution individually.

Such a procedure facilitates the production of individualized dental ceramic articles imitating the natural appearance of a tooth having a rather opaque core (dentin) and a rather translucent shell (enamel).

It has been found that the solution described in the present text is in particular useful for coloring and enhancing the brightness of zirconia articles having been obtained when sintering porous zirconia articles having properties as described in the text below. Especially suitable are porous zirconia articles obtained when heat-treating a zirconia aerogel block.

The brightness and color of the zirconia material after sintering can be adjusted by varying the amount and nature of the coloring ions and the content of bismuth. If, for example, ions with low coloring effect are used, a coloring solution with a huge brightness enhancing effect but a comparable low coloring effect can be provided.

If, for example, ions with a high coloring effect are used, a coloring solution with a high coloring but lower brightness enhancing effect can be provided. This offers the possibility to individually adjust the color and brightness of zirconia ceramic materials and addresses the practitioner's desire to provide high-end aesthetic dental restorations, including highly aesthetic monolithic dental restorations.

According to one embodiment the porous zirconia dental article to be treated with the solution described in the present text can be characterized by at least one or all of the following features:

(a) showing a N2 adsorption and/or desorption of isotherm type IV according to IUPAC classification;
(b) showing a N2 adsorption and desorption with a hysteresis loop,
(c) showing a N2 adsorption and desorption of isotherm type IV according to IUPAC classification and a hysteresis loop,
(d) showing a N2 adsorption and desorption of type IV with a hysteresis loop of type H1 according to IUPAC classification,
(e) showing a N2 adsorption and desorption of type IV with a hysteresis loop of type H1 according to IUPAC classification in a p/p0 range of 0.70 to 0.95;
(f) average connected pore diameter: from about 10 to about 100 nm or from about 10 to about 70 nm or from about 10 to about or from about 10 to about 50 nm or from about 15 to about 40;
(g) average grain size: less than about 100 nm or less than about 80 nm or less than about 60 nm or from about 10 to about 100 or from about 15 to about 60 nm;
(h) BET surface: from about 10 to about 200 $m^2/g$ or from about 15 to about 100 $m^2/g$ or from about 16 to about 60 $m^2/g$;
(i) Biaxial flexural strength: from about 10 to about 40 or from about 15 to about 30 MPa;
(j) x, y, z dimension: at least about 5 mm or at least about 10 or at least about 20 mm;
(k) Vickers hardness: from about 25 (HV 0.5) to about 150 (HV 1) or from about 40 to about 150.

A combination of the following features was found to be particularly beneficial: (a) and (h), or (a) and (b) and (h), or (b) and (c), or (c), (e), (g) and (h). The BET surface of zirconia materials described in the prior art is typically within a range from 2 to 9 $m^2/g$. Thus, the porous zirconia article described in the present text may have a unique combination of features, which facilitates the production of highly aesthetic ceramic articles, especially with respect to translucency.

The average grain size of the zirconia particles in the porous zirconia article described in the present text can be small compared to the average grain size of the material of commercially available mill blanks. A small grain size can be beneficial in that it typically leads to a more homogeneous material (from a chemical perspective), which may also result in more homogeneous physical properties.

Useful ranges for the x, y and z dimensions include from about 5 to about 300 or from about 10 to about 200 mm. The porous zirconia article may have dimensions suitable to be machined by with a machining device. Further, the porous zirconia article may have a flexural strength and/or a Vickers hardness suitable to machine the article by grinding or milling tools.

The average connected pore diameter of the material of the porous zirconia article can be lower compared to the pore diameter of the material commercially available mill blanks are made of (having typically an average connected pore size above about 200 nm). An average connected pore diameter in this range can be beneficial in that it facilitates a quite homogeneous distribution of the solution into the pores of the zirconia article. A small pore diameter typically also results in a comparably huge internal surface and/or a comparably high surface energy. A huge internal surface may enhance the sorption properties of the article.

A huge internal surface, however, often requires an adjustment of the composition and physical properties of the solution to be used for treating the porous zirconia article. If desired the above features can be determined as described in the Example section.

According to one embodiment, the porous zirconia article can be characterized by at least one of the following features:
    ZrO2 content: from about 70 to about 98 mol % or from about 80 to about 97 mol %;
    HfO2 content: from about 0 to about 2 mol % or from about 0.1 to about 1.8 mol %;
    Y2O3 content: from about 1 to about 15 mol % or from about 1.5 to about 10 mol % or from about 2 to about 5 mol %;
    Al2O3 content: from about 0 to about 1 mol % or from about 0.005 to about 0.5 mol % or from about 0.01 to about 0.1 mol %.

According to a further embodiment, the porous zirconia article has a composition being characterized by the following features:
    ZrO2 content: from about 90 to about 98 mol %,
    HfO2 content: from about 0 to about 2 mol %,
    Y2O3 content: from about 1 to about 5 mol %,
    Al2O3 content: from about 0 to about 0.1 mol %.

It was found that a higher Y2O3 content typically leads to an increase of the cubic crystal phase in the zirconia ceramic material after having sintered the material to final density. A higher content of the cubic crystal phase may contribute to a better translucency.

According to an another embodiment the porous zirconia article can be characterized by the at least one or all of the following features:
    showing a N2 adsorption and/or desorption of isotherm type IV according to IUPAC classification, preferably showing a N2 adsorption and desorption with a hysteresis loop in a p/p0 range of 0.70 to 0.95,
    average connected pore diameter: from about 15 to about 60,
    average grain size: less than about 100 nm,
    BET surface: from about 15 to about 100 m²/g or from about 16 to about 60 m²/g.

The porous zirconia article may in addition be characterized by at least one or all of the following features:
    x, y, z dimension: at least about 5 mm,
    Vickers hardness: from about 25 (HV 0.5) to about 150 (HV 1),
    Biaxial flexural strength: from about 10 to about 40 MPa,
    Density: from about 40% to about 60% of theoretical density.

The porous zirconia article showing the above mentioned N2 adsorption and/or desorption properties can be obtained by a process comprising the step of heat treating a zirconia aerogel.

The zirconia aerogel can typically be characterized by at least one or all of the following features:
a. comprising crystalline zirconia particles having an average primary particle size in a range from 2 nm to 50 nm or from about 2 nm to about 30 nm or from about 2 to about 20 or from about 2 to about 15 nm;
b. content of crystalline zirconia particles: at least about 85 mol.-%;
c. having an organic content of at least 3 wt.-% or within a range from about 3 to about 10 wt.-%;
d. x, y, z dimension: at least about 5 or at least about 8 or at least about 10 or at least about 20 mm.

A combination of the features (a) and (b) or (a) and (c) or (a), (b) and (c) can be preferred.

The heat treatment for obtaining the porous zirconia article is typically done under the following conditions:
    temperature: from about 900 to about 1100° C. or from about 950 to about 1090° C.; from about 1000 to about 1080° C.;
    atmosphere: air or inert gas (e.g. nitrogen, argon);
    duration: until a density of about 40% to about 60% of the final density of the material has been reached.

The heat treatment can be conducted in one or more steps. In a first heat treatment step a binder burn-out could be performed to remove all organic additives from previous process steps to obtain a so-called "white body". In a second heat treatment step the strength and/or the hardness of the white-body could be adjusted to the needs of the follow up processes like machining. In case of a machinable blank (e.g. dental mill block) the sintering protocol should reflect the interaction of temperature with strength and/or hardness.

If the temperature is too low, the hardness and/or strength of the resulting article might be too low. This can cause problems during a later machining step, e.g. with respect to chipping. If, on the other hand, the temperature is too high, the hardness and/or strength of the material may become too high. This can cause problems during a later machining step as well, e.g. with respect to the machining tool durability.

The dwell time (that is the time during which the aerogel is kept at that temperature) is not very critical. The dwell time can be zero. The dwell time, however, can also be in a range from about 0 to about 24 h or from about 0.1 to about 5 h. If the dwell time is too long, the dental milling blocks may become too hard to be machined under reasonable conditions.

According to one embodiment, the porous zirconia article showing the above mentioned N2 adsorption and/or desorption properties can be obtained by a process comprising the steps of:
    providing a zirconia sol comprising crystalline metal oxide particles and a solvent,
    optionally concentrating the zirconia sol to provide a concentrated zirconia sol,
    mixing the sol with a polymerizable organic matrix (e.g. adding a reactive surface modifier to the zirconia sol and optionally an initiator being able to polymerizable surface-modified particles of the zirconia sol);
    optionally casting the zirconia sol into a mould to provide a casted zirconia sol, curing the polymerizable organic matrix of the zirconia sol to form a gel (sometimes also referred to as gelation step), removing the solvent from the gel (e.g. by first removing water, if present, from the gel via a solvent exchange process to provide an at least partially de-watered gel; followed by a further extraction step where the remaining solvent is extracted e.g. via super critical extraction) to provide the aerogel, optionally cutting the aerogel into smaller pieces, heat-treating the aerogel to obtain e.g. a machinable material or article.

In certain embodiments the solution described in the present text fulfils at least one or more, sometimes all of the following parameters:

pH value: from about 0 to about 9 or from about 1 to about 8 or from about 2 to about 7;

viscosity: from about 1 to about 10,000 mPa*s or from about 1 to about 6,000 mPa*s or from about 1 to about 2,000 mPa*s (measured at 23° C.).

If desired, these parameters can be determined as outlined in the Example section. If the solution is a water containing (aqueous) solution, it typically has a pH value in the range of 0 to 9, that is from strong acidic to slightly basic.

If the pH value of the solution is outside this range, it might be difficult to achieve a storage stable solution. In particular, the cations of the non-coloring agent might start to precipitate from the solution. If the solution does not contain a complexing agent, a pH value in the acidic range is typically preferred. If the solution, however, contains a complexing agent, the pH value may be in a range from slightly acidic to slightly basic (e.g. 4 to 9 or 5 to 8).

The solution has typically an adequate viscosity so that a sufficient amount of solution can not only be applied to the surface of the zirconia article but also is able to migrate into the pores of the zirconia article. Adjusting the viscosity to a value as indicated above can be beneficial in that the solution can be more accurately applied to particular sections or regions of the porous zirconia article.

If the viscosity of the solution is too high, the solution might not be able to sufficiently enter the pores of the zirconia material. On the other hand, if the viscosity of the solution is too low, the solution might migrate into the pores too rapidly and might diffuse into the whole article. In a further embodiment the solution is transparent.

In a further embodiment, the solution containing the solvent and the coloring ions show light absorption in the range from about 380 to about 780 nm. That means, the solution appears colored to the human eye (in contrast to e.g. water).

The solution also comprises a solvent for the coloring ion(s). If desired, mixtures of different solvents can be used. Suitable solvents include water, alcohols (especially low-boiling alcohols, e.g. with a boiling point below about 100° C.) and ketons. The solvent should be able to dissolve the coloring ions used.

Specific examples of solvents which can be used for dissolving the cations contained in the solution include water, methanol, ethanol, iso-propanol, n-propanol, butanol, acetone, ethylene glycol, glycerol and mixtures thereof.

Typically, the complexing agent is present in the solution in an amount sufficient to dissolve at least the cations of the coloring agent in the solvent or to prevent precipitation of these cations.

The solvent is typically present in an amount sufficient to dissolve the components contained or added to the solvent. The solution comprises at least one coloring agent not being iron. The coloring agent is typically added during the process of producing the solution as a salt comprising cations and anions.

The solution may contain only one of the following coloring ions: ions of Er, Pr, Mn or Tb or a combination thereof: Er and Pr; Er and Mn; Er and Tb; Pr and Mn; Pr and Tb; Mn and Tb; Er, Pr and Mn; Er, Pr and Tb; Er, Mn and Tb; Pr, Mn and Tb, Er, Pr, Mn and Tb.

Praseodymium and terbium possess narrower absorption bands than other coloring ions like Fe. Thus, by using either Pr, Tb or a mixture thereof, a higher yield of fluorescence light can be achieved. Praseodymium as an additive to zirconia produces additional, but sometimes undesired orange fluorescence light, since the desired fluorescence color is blue or blue/green.

Terbium is sometimes preferred over praseodymium, since terbium does not produce a fluorescence of its own and thus does not influence the intended fluorescence color caused by the fluorescing agent (like e.g. Bi). Besides those cations the solution described in the present text may contain in addition coloring agent(s) selected from those listed in the Periodic Table of Elements (in the 18 columns form) and are classified as rare earth elements (including Ce, Nd, Sm, Eu, Gd, Dy, Ho, Tm, Yb and Lu) and/or of the subgroups of the rare earth elements and/or salts of transition metals of the groups 3, 4, 5, 6, 7, 9, 10, 11, as long as they do not influence the fluorescence of the material in a negative way. Elements or ions which annul the desired fluorescence or result in a non-tooth colored sample should not be contained.

Anions which can be used include $OAc^-$, $NO_3^-$, $NO_2^-$, $CO_3^{2-}$, $HCO_3^-$, $ONC^-$, $SCN^-$, $SO_4^{2-}$, $SO_3^{2-}$, gluturate, lactate, gluconate, propionate, butyrate, glucuronate, benzoate, phenolate, halogen anions (fluoride, chloride, bromide) and mixtures thereof. The solution described in the present text contains one or more fluorescing agent(s). A fluorescing agent which was found to be particularly suitable comprises ions of bismuth (Bi). The solution may also contain one or more complexing agent(s).

Adding a complexing agent can be beneficial to improve the storage stability of the solution, accelerate the dissolving process of salts added to the solution and/or increase the amount of salts which can be dissolved in the solution. The complexing agent is typically able to form a complex with the metal ions being present in the solution. The complex formed should be soluble in the solvent. Typically the complex formed is better soluble in the solvent than in water. E.g., the complexing agent can be used in an at least stoichiometric ratio with respect to the molar amount of the ions contained in the coloring agent. Good results can be achieved, if the molar ratio of the complexing agent to the cations of the coloring agent is equal to or greater than about 1 or about 2 or about 3.

If the amount of complexing agent used is too low, the coloring agent might not be dissolved entirely. If the amount of complexing agent used is too high, the excess complexing agent itself might remain unsolved. The complexing agent is usually added as a separate component of the solution. However, it can also be added or be present in form of an anion of the coloring agent. Examples include acetylacetonate, crown ethers, cryptands, ethylenediaminetriacetate and its salts, ethylene diamine tetraacetate and its salts, nitrilotriacetate and its salts, citric acid and its salts, triethylentramine, porphin, poly acrylate, poly asparagate, acidic peptides, phthalocyanin, salicylate, glycinate, lactate, propylendiamine, ascorbate, oxalic acid and its salts and mixtures thereof.

Complexing agents having anionic groups as complexing ligands can be preferred. At least parts of the complexing ligands should be anionic. Complexing agents having only uncharged complexing ligands (or even cationic ligands) like pure amines (e.g. ethylendiamin at pH values at 8 to 14) might not yield sufficiently stable solutions. Typically, the complexing agent is present in the coloring solution in an amount sufficient to dissolve at least the cations of the coloring agent in the solvent or to prevent precipitation of these cations.

The complexing agent can be present in an amount of at least about 1 wt.-% or at least about 5 wt.-% or at least about 10 wt.-% with respect to the amount of the whole composition. There is no specific upper limit, however, usually the amount of complexing agent used does not exceed an amount of about 50 wt.-% or about 40 wt.-% or about 30 wt.-% with respect to the amount of the whole coloring solution. The solution may also contain one or more thickening agent(s).

Certain thickening agent(s) can be characterized by at least one of the following features:
viscosity: from about 1 to about 2,000 mPa*s or from about 100 to about 1,500 mPa*s (measured at 23° C. at a shear rate of 50 s$^{-1}$);
free of polymerizable groups like (meth)acrylate groups, epoxy groups, carbon-carbon unsaturated groups;
not containing elements like S, P.

Thickening agent(s) which can be used include polyol(s) (including polyvinyl alcohol), glycol ether(s) (e.g. PEG 200, PEG 400, PEG 600, diethylene glycol methyl ether, diethylene glycol ethyl ether), di- and polyalcohol(s) (including 1,2-propanediol, 1,3-propanediol, glycerol), glycerol ether, polysaccharide(s), xanthan gum, methyl cellulose and mixtures thereof.

Polyethylene glycols which can be used can be represented by formula (1)

$$R1O-(CH_2-CH_2-O)_m-R1 \quad (1)$$

with R1=H, Acyl, Alkyl, Aryl, Alkylaryl, Polypropylglycol, Poly-THF, preferably H, Acetyl, Methyl, Ethyl, Propyl, Butyl, Hexyl, Octyl, Nonyl, Decyl, Lauryl, Tridecyl, Myristyl, Palmityl, Stearyl, Oleyl, Allyl, Phenyl, p-Alkylphenyl, Polypropyleneglycol, Poly-THF and
m=about 2 to about 100,000, preferably about 10 to about 20,000, more preferably about 20 to about 2,000.

The average molecular weight (Mw) of the polyethylene glycol should be in the range of about 100 to about 5,000,000, preferably in the range of about 500 to about 1,000,000, more preferably in the range of about 1000 to about 100,000. The solution may also contain marker substance(s). Adding a marker substance(s) can be beneficial in order to enhance the visibility of the solution during use, especially, if the solution is transparent and color-less.

Thus, the practitioner can easily determine to which parts of the surface of the zirconia article the solution has already been applied and which parts have not been treated yet and should remain untreated. On the other hand, if the marker substance is an organic substance, the marker substance(s) will be burnt during a later sintering step and thus not be incorporated into the crystal structure of the zirconia article. Examples of marker substance(s) which can be used include food colorants like Riboflavin (E101), Ponceau 4R (E124), Green S (E142). The solution described in the present text may also contain one or more additive(s).

Additives which can be added to the coloring solution include redox-stabilizers (such as methoxy phenol hydrochinone, Topanol A, and mixtures thereof), buffers (such as acetate or amino buffers and mixtures thereof), preservative agents (such as sorbic acid or benzoic acid and mixtures thereof) and mixtures thereof.

There is no need for additive(s) to be present, however, if they are present, they are typically present in an amount which is not detrimental to the purpose to be achieved when applying the solution.

According to one embodiment, the solution does not comprise at least one or all of the following components:
ions of Fe in an amount above about 0.1 wt.-% or above about 0.05 wt.-% or above about 0.03 wt.-% or above about 0.01 wt.-%,
solid particles settling from the solution upon storage for more than about 2 h.

Thus, the solution described in the present text is essentially free of ions of Fe or only may contain unavoidable traces of Fe, which may be present in the raw materials used. Further, the solution does typically also not comprise solid particles which may or will remain on the surface of a zirconia article once the coloring solution is applied to the surface of the zirconia article. Thus, the solution described in the present text is neither a dispersion of solid particles in a solvent nor a slurry.

The solvent(s) may be present in the following amounts:
Lower limit: at least about 15 wt.-% or at least about 20 wt.-% or at least about 30 wt.-%;
Upper limit utmost about 99 wt.-% or utmost about 95 wt.-% or utmost about 90 wt.-%;
Range: from about 15 wt.-% to about 99 wt.-% or from about 30 wt.-% to about 90 wt.-%.

The coloring agent(s) may be present in the following amounts (calculated as ions):
Lower limit: at least about 0.05 wt.-% or at least about 0.2 wt.-% or at least about 0.3 wt.-%;
Upper limit: utmost about 10 wt.-% or utmost about 8 wt.-% or utmost about 5 wt.-%;
Range: from about 0.05 wt.-% to about 10 wt.-% or from about 0.3 wt.-% to about 5 wt.-%.

The fluorescing agent(s) may be present in the following amounts (calculated as ions):
Lower limit: at least about 0.005 wt.-% or at least about 0.02 wt.-% or at least about 0.05 wt.-%;
Upper limit: utmost about 3 wt.-% or utmost about 2 wt.-% or utmost about 1 wt.-%;
Range: from about 0.005 wt.-% to about 3 wt.-% or from about 0.05 wt.-% to about 1 wt.-%.

The complexing agent(s) may be present in the following amounts:
Lower limit: at least about 0.2 wt.-% or at least about 1 wt.-% or at least about 2 wt.-%;
Upper limit utmost about 35 wt.-% or utmost about 25 wt.-% or utmost about 15 wt.-%;
Range: from about 0.2 wt.-% to about 35 wt.-% or from about 2 wt.-% to about 15 wt.-%.

The thickening agent(s) may be present in the following amounts:
Lower limit: at least about 1 wt.-% or at least about 2 wt.-% or at least about 3 wt.-%;
Upper limit utmost about 20 wt.-% or utmost about 15 wt.-% or utmost about 10 wt.-%;
Range: from about 1 wt.-% to about 20 wt.-% or from about 3 wt.-% to about 10 wt.-%.

The marking agent(s) may be present in the following amounts:
Lower limit: at least about 0.001 wt.-% or at least about 0.01 wt.-% or at least about 0.1 wt.-%;
Upper limit utmost about 2 wt.-% or utmost about 1 wt.-% or utmost about 0.5 wt.-%;
Range: from about 0.001 wt.-% to about 2 wt.-% or from about 0.1 wt.-% to about 0.5 wt.-%.

The additive(s) may be present in the following amounts:
Lower limit: at least about 0.001 wt.-% or at least about 0.01 wt.-% or at least about 0.1 wt.-%;
Upper limit: utmost about 5 wt.-% or utmost about 2 wt.-% or utmost about 1 wt.-%;
Range: from about 0.001 wt.-% to about 5 wt.-% or from about 0.1 wt.-% to about 1 wt.-%.

Unless defined otherwise, wt.-% is based on the amount of the whole solution.

Further, unless defined otherwise, wt.-% is calculated on the weight of the agent.

The wt.-% given for the coloring agent and fluorescing agent is based on the amount of the metal ion(s) contained in the agent.

Thus, the components contained in the solution described in the present text may be present in the following amounts:
Solvent(s): from about 15 wt.-% to about 99 wt.-% or from about 30 wt.-% to about 90 wt.-%;
Coloring Agent(s): from about 0.05 wt.-% to about 10 wt.-% or from about 0.5 wt.-% to about 5 wt.-% (calculated with respect to the metal ions);
Fluorescing Agent(s): from about 0.005 wt.-% to about 3 wt.-% or from about 0.05 wt.-% to about 1 wt.-% (calculated with respect to the metal ions);
Complexing Agent(s): from about 0.2 wt.-% to about 35 wt.-% or from about 2 wt.-% to about 15 wt.-%;
Thickening Agent(s): from about 1 wt.-% to about 20 wt.-% or from about 3 wt.-% to about 10 wt.-%;
Marking Agent(s): from about 0.001 wt.-% to about 2 wt.-% or from about 0.1 wt.-% to about 0.5 wt.-%;
Additive(s): from about 0.001 wt.-% to about 5 wt.-% or from about 0.1 wt.-% to about 1 wt.-%.

According to a preferred embodiment, the solution described in the present text comprises:
water as solvent in an amount of 20 to 95 wt.-%,
coloring agent(s) comprising metal ions selected form ions of Tb, Er, Mn or combinations thereof in an amount of 0.2 to 8 wt.-% (calculated with respect to the metal ions);
fluorescence agent comprising Bi ions in an amount of 0.02 to 2 wt.-% (calculated with respect to the metal ion);
the solution not comprising Fe ions in an amount above 0.05 wt.-%,
the solution not comprising ions selected from Dy, Nd, Sm, Eu in an amount above about 0.1 wt.-%,
wt.-% with respect to the weight of the solution,
the solution having a pH value in the range of 0 to 9,
the solution having a viscosity in the range of 1 to 2,000 mPa*s at 23° C.

The solution can be produced by mixing its components. This can be done at room temperature or by applying heat and/or while stirring. Applying heat and/or stirring can be beneficial in order to accelerate the dissolution process of the coloring agent into the solvent. The composition is typically stirred until the cations of the coloring agent are completely dissolved in the solvent. If desired, additives (like those mentioned above) can be added. Undesired precipitations can be removed by filtering. The invention is also directed to a kit of parts.

The kit of parts comprises or consists of:
a solution as described in the present text, the solution being preferably be contained in a device as described in the present text,
a porous zirconia dental article as described in the present text,
optionally application equipment, and
optionally an instruction of use.

Examples of application equipment which can be included in the kit of parts described in the present text include brushes, sponges, (hollow) needles, pens, and mixing appliances. Examples of mixing appliances include mixing wells, trays, plates and slides.

The kit of parts may also contain an instruction of use instructing the practitioner how to apply the solution to the porous zirconia dental article and optionally also how to sinter the colored zirconia dental article to final density, if desired. The invention is also directed to a device comprising a reservoir and an opening, the reservoir containing the solution as described in the present text. The device may have the shape of a vessel, bottle or flask.

According to a particular embodiment, the device may have the shape of a pen, the pen comprising a housing, a brush tip, a removable cap and a reservoir for storing the solution described in the present text. The brush tip is typically attached or fixed to the front end of the housing. The reservoir is typically fixed or attached to the rear end of the housing. The removable cap is typically used for protecting the brush tip during storage. Using a pen may facilitate the application of the coloring solution and will help the practitioner to save time.

Currently, coloring solutions are usually offered in bottles and are applied to porous ceramics with a separate brush or even by dipping the entire ceramic into the coloring solution. This often goes along with a lot of waste of the coloring solution. By using a pen, there will be essentially no waste of the coloring solution. Further, a pen with a cap will prevent the pen from drying out if not used. Providing individual pens for individual solutions may further facilitate the application of the composition to the surface of porous dental ceramic(s). Until now, usually only one brush is used and that brush has to be cleaned thoroughly before a further solution is applied.

If, however, one pen for one color is provided, switching the colors during the application process is quite easy and more save for the dental technician, while mixing of different colors using this kind of equipment is still possible by subsequent application of different colors to the ceramic surface. The volume of the reservoir may be in a range from about 1 ml to about 10 ml or from about 2 ml to about 5 ml. The reservoir may be removable or fixed to the housing of the pen.

According to one embodiment, the reservoir is exchangeable. The exchangeable reservoir may have the shape of a cartridge or bullet. The brush tip typically comprises bristles. The material the bristles are made of can be selected from artificial or natural materials. Artificial materials include polyamides (nylon), polyesters and mixtures thereof. Natural materials usually include different kinds of animal hair. The brush tip may be removable or exchangeable, too.

The length of the brush tip extending from the pen is typically within a range from about 5 to about 20 mm or from about 8 to about 15 mm. If the bristles are too short, application of the solution to the inside of a dental restoration may be difficult. If, on the other hand, the bristles are too long, the handling of the brush itself might become impractical for dental applications. The thickness of the brush tip at its base is typically in the range from about 0.3 to about 5 mm or from about 1 to about 4 mm. If the tip is too broad, application of the solution to the inside of a dental restoration may be difficult. If, on the other hand, the tip is too narrow, the handling of the brush itself might become impractical for dental applications.

Furthermore, if the length and the thickness of the brush tip is either too low or too high, it will be difficult to apply the solution properly, that is either too little to too much of the solution is applied. Both may be detrimental for achieving an accurately colored dental ceramic. The shape of the brush tip should be tapered and fan out, if desired, when pressure is applied. Thus, the brush tip should have some flexibility. A brush tip with these properties can be used to draw thin lines and also to paint on larger areas.

A combination of a brush tip comprising bristles having a length from about 8 to about 15 mm with the solution described in the present text having a viscosity above about 200 mPa*s or above about 500 mPa*s (measured at 23° C.) was found to be beneficial. Such a combination facilitates the accurate application of the solution on the surface of the porous dental ceramic(s). Thus, the invention is also directed to a pen as described in the present text comprising the solution.

According to one embodiment, the solution is used for being selectively applied to parts of the surface of a zirconia dental article. That is, the solution is only applied to parts of the surface of the article but not to the whole surface. According to another embodiment the solution is used for being applied the whole surface of the zirconia dental article. This can be achieved, e.g. by dipping the zirconia article completely into the solution.

The invention is also directed to a method for coloring and enhancing the brightness of a zirconia dental article, the method comprising the steps of
  providing a porous zirconia dental article as described in the present text and a coloring solution as described in the present text,
  applying the solution to the porous zirconia article,
  optionally drying the porous zirconia article to which the solution has been applied,
  sintering the porous zirconia article to obtain an at least partially colored zirconia ceramic dental article, The porous zirconia article is typically in a pre-sintered stage. Such an article has usually open pores and thus can be described as absorbent. Selectively applying the solution to the surface of the porous zirconia article is usually achieved by painting e.g. using a brush. However, the solution can also be applied by using a sponge, a fabric, brush-pen or by spraying, equipment which is described in more detail above. The zirconia article is usually treated with the solution for about 0.5 to about 5 minutes, preferably from about 1 to about 3 minutes at room temperature (about 23° C.). Preferably no pressure is used.

A penetration depth of the solution into the article of about 5 mm is considered to be sufficient. The penetration depth can be determined as follows:

A plastic mesh (mesh size 500 μm) is located in a flat cup, which is filled with a colouring solution containing in addition a certain amount of a colourant (e.g. 100 ppm of Rhodamin B). A test bar of a presintered ceramic (LAVA™ Frame; 3M ESPE) having a size of 0=about 24 mm, height=30 mm is placed on the plastic mesh and is soaked with the colouring solution for 2 min; dipping depth: 5 mm. The ceramic is taken out of the solution and is cut into slices. The cutting edges are finished and the penetration of the solution into the ceramic is analysed with a fluorescence microscope. If the added colourant can be detected over the whole range of the dipping depth and not only in a small border area (about 2 mm), the penetration behaviour of the solution is considered to meet the practitioner's needs.

Drying the treated ceramic article is not absolute necessary, but can be preferred to reduce the time needed for firing and to avoid undesired inhomogenous colour effects. Drying can be effected by simply storing the article on a surface at ambient conditions for a couple of hours (about 1 to about 3 hours).

According to one embodiment the zirconia dental article has the shape of a crown, bridge, inlay, onlay, veneer, facing, coping, crown and bridged framework, implant, abutment, orthodontic appliances (e.g. brackets, buccal tubes, cleats and buttons), dental mill blank and parts thereof and parts thereof. If, however, a high boiling solvent is used, drying might be difficult to achieve. The solution and the porous zirconia article described in the present text are in particular useful for producing a dental ceramic article out of a monolithic block. Producing a dental ceramic article out of a monolithic zirconia block has to address the need for translucency in the dental appliance, which is usually met by a fluorescing veneering material. Since this is not possible when using monolithic zirconia, a solution offering high fluorescence intensity in the presence of coloring agents may be even more desired.

The invention is also directed to the zirconia article obtainable or obtained according to the process described in the present text. Such an article is typically characterized by comprising colored sections or being completely colored and showing fluorescence caused by the presence of the fluorescent agent(s) having migrated into the pores of the porous zirconia dental article before sintering. The heat treatment for obtaining the sintered zirconia dental article is typically done under the following conditions:
  temperature: from about 900 to about 1500° C. or from about 1000 to about 1400° C. or from about 1100 to about 1350° C. or from about 1200 to about 1400° or from above about 1300 to about 1400° C. or above about 1320° C. to about 1400° C. or above about 1340° C. or above about 1350° C.;
  atmosphere: air or inert gas (e.g. nitrogen, argon);
  pressure: ambient pressure;
  duration: until a density of about 95 to about 100% of the final density of the material has been reached.

The dwell time (that is the time during which the article is kept at that temperature) is not really critical. The dwell time can be zero. The dwell time, however, can also be in a range from about 0 to about 24 h or from about 0.1 to about 5 h. If desired, the solution described in the present text can also be provided as a kit of parts comprising a receptacle containing a coloring liquid (A) and a receptacle containing a fluorescence liquid (B), the coloring liquid (A) comprising a solvent and coloring agent comprising ions selected from Tb, Er, Pr, Mn and combinations thereof, the fluorescing liquid (B) comprising a solvent and fluorescing agent comprising ions of Bi, the mixture of the coloring liquid (A) and the fluorescing liquid (B) not comprising Fe ions in an amount above about 0.05 wt.-% with respect to the weight of the mixture. The solvent can be any of the solvent(s) described above. Further, liquid (A) and liquid (B) can contain any of the other optional components described above. In addition, the kit can contain, any of the other optional components described above including an instruction of use, if desired. The receptacle can have any shape useful for storing the liquid(s). Useful receptacles include the devices mentioned above for storing the solution described in the present text, including a brush pen. Liquid (A) and liquid (B) described above can be used as follows:

According to one embodiment, liquid (A) and liquid (B) are mixed to obtain the solution described in the present text and applied as mixture to at least parts of the surface of a porous dental ceramic. According to another embodiment, in a first step liquid (A) is applied to the surface of the porous dental ceramic to be treated. In a further step, liquid (B) is applied to at least those parts of the surface of the porous dental ceramic which have already been treated with liquid (A).

According to another embodiment, in a first step liquid (B) is applied to the surface of the porous dental ceramic to be treated. In a further step, liquid (A) is applied to at least parts of the surface of the porous dental ceramic which has already been treated with liquid (B). The solution described in the present text does typically not contain components which might produce a toxic, injurious, or immunological response in living tissue or components or additives which jeopardize the intended purpose to be achieved with the present invention, especially in the sintered ceramic. Thus, for example components or additives added in an amount which finally (e.g. after a sintering step) results in a non-tooth-colored article are usually not contained in the final dental restoration. Typically, an article is characterized as tooth colored if it can be allocated a color from the Vita™ color code system, known to the person skilled in the art.

The solution does typically also not comprise insoluble pigments or insoluble additives or inorganic thickening agents like silica (e.g. Aerosil) etc. Moreover, if possible, the solution should not or only contain a small amount of ingredients which can be detrimental to the firing equipment during the sintering process. According to a further embodiment, the solution does not contain glass or glass/ceramic particles.

The production of the zirconia material which can be treated with the solution described in the present text does typically also not require the application of a hot isostatic pressing step (HIP). The complete disclosures of the patents, patent documents, and publications cited herein are incorporated by reference in their entirety as if each were individually incorporated. The following examples are given to illustrate, but not limit, the scope of this invention.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).
Measurements
Ion Concentration If desired, the concentration of ions in the solution can be determined by X-ray fluorescence sprectrometry (XRF). Some XRF devices offer the possibility to directly measure ion concentrations in liquid solutions, e.g. the ZSX Primus II from Rigaku, Japan.
Fluorescence The fluorescence properties can be determined using an optical setup comprising the following parts (particularly suited for sharp emission bands): GC America G-Light as light source, irradiating light of around 409 nm wavelength, an Ulbricht sphere, fiber optics from Topsensor Systems as light conductor and an A/D converter. A sample having the shape of a disc (diameter>10 mm, thickness of 1.0 mm) can be used to cover the opening of the Ulbricht sphere. The light emission spectrum of the sample can be measured while trans-illuminating it with exitation radiation (violet light). Excitation radiation of shorter wavelengths is also suited for fluorescence measurements.

Another option is to measure the remission spectrum of the samples e.g. with a spectrophotometer (e.g. Colour i7; X-Rite). Typically two measurements are done: one remission spectrum using irradiation e.g. of the D65 light source including the UV range and one remission spectrum with irradiation e.g. of the D65 light source excluding the UV range. Subsequently both spectra are subtracted from each other, the yielding curve showing the fluorescence effect(s). The area between 410 nm and 540 nm is defined as the area of fluorescence, while the area between 550 nm and 710 nm is defined as the background. The signal intensity of the background area is subtracted from the signal intensity of the fluorescence area to obtain the relative fluorescence intensity. Choosing this measurement method can be preferred, because it also yields color information about the sample (i.e. L*a*b* values).

Alternatively, the samples can be placed in an UV-light box used for inspection of e.g. thin layer chromatography plates. If desired, fluorescence can be detected by the human eye as by the lightening up of the sample against the black background.
pH-Value If desired, the measurement of the pH-value can be achieved by means known by the person skilled in art. E.g. an instrument like Metrohm™ 826 or pH indicator paper can be used.
Viscosity If desired, the measurement of the viscosity can be done as follows: A viscosimeter MCR300 (from Anton Paar Comp.) is used. A portion of the composition is placed between two steel discs with a diameter of 8 mm and a gap of 1 mm at a temperature of 23° C. The gap is filled completely with the composition. Excess composition is removed. The shear rate between the rotating discs d(gamma)/dt is set constantly to 50 s$^{-1}$. The measurement is done 500 s after starting the shearing process of the composition.
Method for Measuring N2 Sorption Isotherms, BET Surface Area, Pore Volume, Average Connected Pore Diameter If desired, the above mentioned properties can be determined as follows:

The samples are run on either a QUANTACHROME AUTOSORB-1 BET Analyzer" (Quantachrome Instruments, Boynton Beach, Fla.) or a BELSORP-mini instrument (BEL Japan Inc., Osaka, Japan). The samples are weighed and outgassed at 200° C. for two days then subjected to a N2 sorption process with an appropriate number and distribution of measurement points, e.g. 55 adsorb points and 20 desorb points from a $P/P_o$ range $1 \times 10^6$ to 1 and back to 0.05 giving full isotherms. The specific surface area S is calculated by the BET method (Details regarding calculation see Autosorb-1 Operating Manual Ver. 1.51 IV. Theory and Discussion, Quantachrome Instruments, Inc.). The total pore volume $V_{liq}$ is derived from the amount of vapor adsorbed at a relative pressure close to unity ($P/P_o$ closest to 1), by assuming that the pores are then filled with liquid adsorbate (Details regarding calculation see Autosorb-1 Operating Manual Ver. 1.51 IV. Theory and Discussion, Quantachrome Instruments, Inc.). The average pore diameter (d) is calculated from the surface area (S) and the total pore volume ($V_{liq}$):

$$d = \frac{4 V liq}{S}.$$

Average Grain Size

If desired, the average grain size can be determined with the Line Intercept Analysis. FESEM micrographs with 70,000 times magnification are used for grain size measurement. Three or four micrographs taken from different areas of the sintered body are used for each sample. Ten horizontal lines, which are spaced at roughly equal intervals across the height of each micrograph, are drawn. The numbers of grain boundary intercepts observed on each line are counted and used to calculate the average distance between intercepts. The average distance for each line is multiplied by 1.56 to determine the grain size and this value is averaged over all the lines for all micrographs of each sample.

Density

If desired, the density of the sintered material can be measured by an Archimedes technique. The measurements is made on a precision balance (identified as "AE 160" from Mettler Instrument Corp., Hightstown, N.J.) using a density determination kit (identified as "ME 33360" from Mettler Instrument Corp.). In this procedure the sample is first weighed in air (A), then immersed in water (B). The water is distilled and deionized. One drop of a wetting agent (obtained under trade designation "TERGITOL-TMN-6" from Dow Chemical Co., Danbury, Conn.) is added to 250 ml of water. The density is calculated using the formula $\rho = (A/(A-B)) \rho 0$, where $\rho 0$ is the density of water. The relative density can be calculated by reference to the theoretical density ($\rho t$) of the material, $\rho_{rel} = (\rho/\rho t) 100$.

Vickers Hardness

If desired, the Vickers hardness can be determined according to ISO 843-4 with the following modifications: The surface of the samples are ground using silicon carbide grinding paper (P400 and P1200). The test forces are adjusted to the hardness level of samples. Used test forces were between 0.2 kg and 2 kg and were applied for 15 s each indentation. A minimum of 10 indentations is measured to determine the average Vickers hardness. The tests can be conducted with a hardness tester Leco M-400-G (Leco Instrumente GmbH).

Biaxial Flexural Strength

If desired, the biaxial flexural strength can be determined according to ISO 6872 (2008) with the following modifications: The sample is sawn into wafers with a thickness of 1 to 2 mm using a dry cut saw. The diameter of the samples should be between 12 and 20 mm. Each wafer is centred on a support of three steel balls with a support diameter of 14 mm. The punch diameter in contact with the wafer is 3.6 mm. The punch is pushed onto the wafer at a rate of 0.1 mm per min. A minimum of 6 samples is measured to determine the average strength. The tests can be conducted in an Instron 5566 universal testing machine (Instron Deutschland GmbH).

Materials Used

TABLE 1

| Name | Description |
| --- | --- |
| diammonium EDTA | complexing agent |
| triammonium citrate | complexing agent |
| bismuth acetate | fluorescing agent |
| PEG 35000 | Polyethylene glycol MW 35,000; thickening agent |
| terbium acetate hydrate | coloring agent |
| praseodymium acetate hydrate | coloring agent |
| ammonium iron citrate | coloring agent |
| Lava ™ Plus zirconia material | zirconia material (available from 3M ESPE) |
| Zirconia aerogel | zirconia material |
| Zirconium(IV) acetate | An aqueous solution of zirconium acetate containing nominally 16.3 wt.-% Zr. The aqueous solution was exposed to an ion exchange resin (obtained under the trade designation "AMBERLYTE IR 120" from Rohm and Haas Company, Philadelphia, PA) before use (oxide content 21.85 wt.-%). |
| DI water | De-ionized water |
| Yttrium(III) acetate | Yttrium (III) acetate tetrahydrate (oxide content 33.4 wt.-%) |
| Lanthanum(III) oxide | Lathanum (III) oxide (oxide content 99.45 wt.-%) |
| HEMA | 2-Hydroxyethyl methacrylate |

The solutions described in the present text were tested on two different kinds of zirconia material, a commercially available zirconia material and a zirconia material which is based on a pre-sintered aerogel.

General Procedure—Preparation of Zirconia Aerogel Sample

The zirconia aerogel sample was prepared as described in the Example Section of European Patent Application # EP12196633.7 filed on Dec. 12, 2012 (pages 38-42).

Preparation of $ZrO_2$ (88 mol-%)/$Y_2O_3$ (12 mol-%) Sol (Sol C1)

Sol compositions are reported in mole percent inorganic oxide. Sol C1 was prepared as follows: (All other sols were prepared by similar methods in similar equipment.)

A hydrothermal reactor was prepared from 15 meters of stainless steel braided smooth tube hose (0.64 cm inside diameter, 0.17 cm thick wall; obtained under the trade designation "DUPONT T62 CHEMFLUOR PTFE" from Saint-Gobain Performance Plastics, Beaverton, Mich.). This tube was immersed in a bath of peanut oil heated to the desired temperature. Following the reactor tube, a coil of an additional 3 meters of stainless steel braided smooth tube hose ("DUPONT T62 CHEMFLUOR PTFE"; 0.64 cm I.D., 0.17 cm thick wall) plus 3 meters of 0.64 cm stainless-steel tubing with a diameter of 0.64 cm and wall thickness of 0.089 cm that was immersed in an ice-water bath to cool the material and a backpressure regulator valve was used to maintain an exit pressure of 2.76 MPa.

A precursor solution was prepared by combining the zirconium acetate solution (2.000 grams) with DI water (2205.3 grams). Yttrium acetate (327.8 grams) was added while mixing until full dissolution. The solids content of the resulting solutions was measured gravimetrically (120° C./hr. forced air oven) to be 22.16 wt.-%. D.I. water (718 grams) was added to adjust the final concentration to 19 wt.-%. This procedure was repeated three times to give a total of about 15.115 grams of precursor material. The resulting solution was pumped at a rate of 11.48 ml/min. through the hydrothermal reactor. The temperature was 225° C. and the average residence time was 42 min. A clear and stable zirconia sol was obtained.

Table 2 is a summary of the compositions prepared and the process conditions used for other sols produced in a similar manner as Sol C1.

TABLE 2

| Sol | $ZrO_2$ [mol %] | $Y_2O_3$ [mol %] | $La_2O_3$ [mol %] | Residence time [min] | Temperature [° C.] |
|---|---|---|---|---|---|
| T1 | 97.7 | 2.3 | 0 | 42 | 207 |
| C1 | 88 | 12 | 0 | 42 | 225 |
| C2 | 88 | 12 | 0 | 42 | 207 |
| S1 | 93.5 | 5 | 1.5 | 42 | 225 |

Sol Concentration and Diafiltration

The resulting sols were concentrated (20-35 wt.-% solids) first via ultrafiltration using a membrane cartridge (obtained under the trade designation "M21S-100-01P" from Spectrum Laboratories Inc., Rancho Dominguez, Calif.), and then via constant volume diafiltration using the same membrane cartridge. The resulting sol was then further concentrated via rotary evaporation.

Gel Preparation

The gels were prepared by combining the T and C sols to obtain the desired oxide composition and adjusting the oxide, acetic acid and solvent composition via diafiltration, distillation or a combination thereof. Sol S1 was prepared with one desired oxide composition, so that no further mixing of sols was required. Only acetic acid and solvent composition were adjusted via diafiltration, distillation or a combination thereof.

The acrylic acid, HEMA and initiator were added, the sol placed in a mold and thermally cured at 50° C. for 4 hours. A typical procedure is given for G1 below. The composition of the all the gels are given in Table 3 (the solvent is made up of water and ethanol).

Example G1

A 141.1 g sample of Sol C1 (prepared and diafiltered and concentrated as described above, 30.4 wt.-% oxide and 3.02 wt.-% acetic acid) and 400 g of Sol T1 (prepared and diafiltered and concentrated as described above, 44.2 wt.-% oxide and 2.30 wt.-% acetic acid) were charged in to a 1000 ml RB flask. Water (133.3 g) was removed via rotary evaporation resulting in viscous somewhat dry material. Ethanol (121.2 g), acrylic acid (23.13 g), HEMA (11.8 g) were added to the flask. The contents were stirred overnight resulting is a fluid translucent sol. 2,2'-azobis(2-methylbutyronitrile) ("VAZO 67") (1.2 g) was added and stirred until dissolved. The contents of the flask were then purged with $N_2$ gas for 21 min. The sample (translucent and low viscosity) was charged to cylindrical containers (29 mm diameter). Each container was about 18 ml in volume and each was sealed on both ends (very little air gap was left between the top and liquid). The samples were allowed to stand for about 1 h then placed in an oven to cure (50° C., 4 h). This resulted in a clear translucent blue gel. The gel was removed from the container and placed in a 473 ml wide mouth jar (three gels per jar). The jar was filled with ethanol (275 g, denatured). The sample was soaked for 24 h then the ethanol was replaced with fresh ethanol. The sample was soaked for 24 h then the ethanol was replaced with a third batch of fresh ethanol. The sample was allowed to soak until the supercritical extraction was done. The above manipulations were done minimizing the amount of time the gel was exposed to the air.

Table 3 is a summary of the gel production conditions used for other gels produced in a similar manner to Example G1.

TABLE 3

| | sol(s) used | T-sol:C-sol (wt.-%) | Oxide (wt.-%) | Acetic acid (wt.-%) | Acrylic acid (wt.-%) | Hema (wt. %) | Solvent |
|---|---|---|---|---|---|---|---|
| G-1 | T1:C1 | 75.54:24.45 | 39.33 | 3.34 | 4.14 | 2.13 | 51.06 |
| G-2 | T1:C2 | 75.51:24.48 | 39.99 | 5.92 | 4.24 | 2.17 | 46.94 |
| G-3 | T1:C2 | 60.67:39.33 | 39.80 | 6.02 | 4.24 | 2.17 | 46.98 |
| G-4 | S1 | n.a. | 40.41 | 2.36 | 4.24 | 2.17 | 50.82 |

Extraction Process

The gels were loaded into the supercritical extractor. The wet $ZrO_2$-based gels were removed separately from the ethanol bath, weighed, placed individually inside small canvas pouches, and then stored briefly in another ethanol bath before being loaded into the 10-L extractor vessel. For extraction of the gels, about 3500 ml of 200-proof ethanol was added to the 10-L extractor of a laboratory-scale supercritical fluid extractor unit. The canvas bags containing the wet zirconia-based gels were transferred from the ethanol bath into the 10-L extractor so that the wet gels were completely immersed in the liquid ethanol inside the jacketed extractor vessel, which was heated and maintained at 60° C. After the extractor vessel lid was sealed in place, liquid carbon dioxide was pumped by a chilled piston pump (setpoint: −12.5° C.) through a heat exchanger to heat the $CO_2$ to 60° C. and into the 10-L extractor vessel until an internal pressure of 11.0 MPa was reached. At these conditions, carbon dioxide is supercritical. Once the extractor operating conditions of 11 MPa and 60° C. were met, a PID-controlled needle valve regulated the pressure inside the extractor vessel by opening and closing to allow the extractor effluent to pass through a porous 316L stainless steel frit (obtained from Mott Corporation as Model #1100S-5.480 DIA-0.062-10-A), then through a heat exchanger to cool the effluent to 30° C., and finally into a 5-L cyclone separator vessel that was maintained at room temperature and pressure less than 5.5 MPa, where the extracted ethanol and gas-phase $CO_2$ were separated and collected throughout the extraction cycle for recycling and reuse. Supercritical carbon dioxide (scCO$_2$) was pumped continuously through the 10-L extractor vessel for 7 hours from the time the operating conditions were achieved. After the 7-hour extraction cycle, the extractor vessel was slowly vented into the cyclone separator over 16 hours from 11 MPa to atmospheric pressure at 60° C. before the lid was opened and the dried canvas pouches containing the aerogel were removed. The dry aerogels were removed from their canvas pouches, weighed, and transferred into 237 ml glass jars packed with tissue paper for storage.

Burnout/De-Binder Process

The extracted aerogel samples from above were removed from their closed container and set on an aluminium oxide plate, covered with aluminium oxide cylinders and fired in air according to the following schedule in a chamber furnace ("Nabertherm 60 liter"): i—heat from 20° C. to 220° C. at 18° C./h rate; ii—heat from 220° C. to 244° C. at 1° C./h rate; iii—heat from 244° C. to 400° C. at 6° C./h rate; iv—heat from 400° C. to 900° C. at 60° C./h rate; v—hold at 900° C. for 2 h and vi—cool down from 900° C. to 20° C. at 600° C./h rate. After burnout process, the samples were crack free.

Pre-Sintering Process

The de-bindered discs were set on an aluminium oxide plate and fired in air according to the following schedule in a chamber furnace (Nabertherm 1 liter): i—heat from 20° C. to 900° C. at 10° C./min. rate; ii—heat from 900° C. to 1020° C. at 2° C./min. iii—hold at 1020° C. for 2 hours and iv—cool down from 1020° C. to 600° C. in 1 h. Pre-sintering steps were finished when furnace was cooled down to room temperature. The zirconia aerogel block was cut into discs (diameter: 13 mm; height: 1.5 mm).

General Procedure—Preparation of Solution

A Solution (A) was prepared by dissolving 12.00 g bismuth acetate and 11.16 g diammonium EDTA in 120.00 g de-ionized water. Solution (A) was combined with further components as outlined below.

Reference Example 1 (Full Fluorescence)

A Composition (I) containing 8.60 g de-ionized water, 0.80 g PEG 35000 and 0.60 g of Solution (A) was prepared. A pre-sintered disc of a zirconia aerogel was infiltrated with Composition (I) for 2 min and then left to dry for 3 h. The dried disc was sintered at 1300° C. for 2 h.

Reference Example 2 (No Fluorescence)

A pre-sintered, uncolored disc of a zirconia aerogel was sintered at 1300° C. for 2 h.

Inventive Example 1

A Composition (II) containing 8.44 g de-ionized water, 0.80 g PEG 35000, 0.06 g terbium acetate hydrate, 0.10 triammonium citrate, and 0.60 g of Solution (A) was prepared. A pre-sintered disc of a zirconia aerogel was infiltrated with Composition (II) for 2 min and then left to dry for 3 h. The dried disc was sintered at 1300° C. for 2 h and the fluorescence of the obtained ceramic was checked together with all other samples under UV light.

Inventive Example 2

A Composition (III) containing 8.45 g de-ionized water, 0.80 g PEG 35000, 0.05 g praseodymium acetate hydrate, 0.10 triammonium citrate and 0.60 g of Solution (A) was prepared. A pre-sintered disc of a zirconia aerogel was infiltrated with Composition (III) for 2 min and then left to dry for 3 h. The dried disc was sintered at 1300° C. for 2 h and the fluorescence of the obtained ceramic was checked together with all other samples under UV light.

Comparative Example 1

A Composition (IV) containing 8.56 g de-ionized water, 0.80 g PEG 35000, 0.04 g ammonium iron citrate, and 0.60 g of Solution (A) was prepared. A pre-sintered disc of a zirconia aerogel was infiltrated with this composition for 2 min and then left to dry for 3 h. The dried disc was sintered at 1300° C. for 2 h and the fluorescence of the obtained ceramic was checked together with all other samples under UV light.

Analysis

The samples prepared were analyzed with respect to their fluorescent properties.

Results

Visual Impression

Reference Sample 1: intensive blue fluorescence
Reference Sample 2: violet reflection from visible wavelengths of the UV lamp on the white sample
Inventive Example 1: visible green fluorescence
Inventive Example 2: visible orange fluorescence
Comparative Example: no fluorescence or reflection visible, sample appears dark Measurements

TABLE 4

| Sample | L* | a* | b* | Rel. fluorescence intensity [%] | Fluorescence maximum [nm] |
| --- | --- | --- | --- | --- | --- |
| Ref. Sample 1 | 77.84 | −3.31 | 1.85 | 100 | 440 (blue) |
| Ref. Sample 2 | 77.14 | −3.62 | 0.33 | 12 | none |
| Inv. Example 1 | 77.51 | −3.85 | 12.27 | 85 | 440 (blue) |
| Inv. Example 2 | 77.27 | −3.58 | 15.80 | 129 | 450 (blue) |
|  |  |  |  |  | 630 (orange/red) |
| Comp. Example 1 | 81.24 | −3.20 | 15.14 | 39 | none |

Commercially available Zirconia Material

General Procedure—Preparation of Solution

A fluorescence liquid was prepared using 120.00 g de-ionized water, 12.00 g bismuth acetate and 11.16 g diammonium EDTA.

General Procedure—Preparation of Dental Article

Commercially available Lava™ Plus zirconia material (3M ESPE) was used to prepare the samples to be colored. The Lava™ Plus zirconia material was removed from the blank holder and cut into discs (diameter: 12 mm; height: 2 mm).

Reference Sample 1 (Full Fluorescence)

A Composition (V) containing 8.60 g de-ionized water, 0.80 g PEG35000 and 0.60 g of fluorescence liquid was prepared. A pre-sintered disc of a Lava™ Plus zirconia (3M ESPE) was infiltrated with this composition for 2 minutes and then left to dry for 3 hours. The dried disc was sintered at 1450° C. for 2 hours.

Reference Sample 2 (No Fluorescence)

A pre-sintered, uncolored disc of a Lava™ Plus zirconia (3M ESPE) was sintered at 1450° C. for 2 hours.

Inventive Example 1

A Composition (VI) containing 8.44 g de-ionized water, 0.80 g PEG35000, 0.06 g terbium acetate hydrate, 0.10 triammonium citrate and 0.60 g of fluorescence liquid was prepared. A pre-sintered disc of a Lava™ Plus zirconia (3M ESPE) was infiltrated with this composition for 2 minutes and then left to dry for 3 hours. The dried disc was sintered at 1450° C. for 2 hours.

Inventive Example 2

A Composition (VII) containing 8.45 g de-ionized water, 0.80 g PEG35000, 0.05 g praseodymium acetate hydrate, 0.10 triammonium citrate and 0.60 g of fluorescence liquid was prepared. A pre-sintered disc of a Lava™ Plus zirconia (3M ESPE) was infiltrated with this composition for 2 minutes and then left to dry for 3 hours. The dried disc was sintered at 1450° C. for 2 hours.

Comparative Example 1

A Composition (VIII) containing 8.56 g de-ionized water, 0.80 g PEG35000, 0.04 g ammonium iron citrate and 0.60 g of fluorescence liquid was prepared. A pre-sintered disc of a Lava™ Plus zirconia (3M ESPE) was infiltrated with this composition for 2 minutes and then left to dry for 3 hours. The dried disc was sintered at 1450° C. for 2 hours.

Comparative Example 2

A Composition (IX) containing 9.04 g de-ionized water, 0.80 g PEG35000, 0.06 g terbium acetate hydrate, 0.10 triammonium citrate and no fluorescence liquid was prepared. A pre-sintered disc of a Lava™ Plus zirconia (3M ESPE) was infiltrated with this composition for 2 minutes and then left to dry for 3 hours. The dried disc was sintered at 1450° C. for 2 hours.

Comparative Example 3

A Composition (X) containing 9.05 g de-ionized water, 0.80 g PEG35000, 0.05 g praseodymium acetate hydrate, 0.10 triammonium citrate and no fluorescence liquid was prepared. A pre-sintered disc of a Lava™ Plus zirconia (3M ESPE) was infiltrated with this composition for 2 minutes and then left to dry for 3 hours. The dried disc was sintered at 1450° C. for 2 hours.

Results
Visual Impression
Reference Sample 1: intensive blue fluorescence.
Reference Sample 2: violet reflection from visible wavelengths of the UV lamp on the white sample
Inventive Example 1: visible green fluorescence
Inventive Example 2: visible orange fluorescence
Comparative Example 1: no fluorescence and very little reflection visible, sample appears dark
Comparative Example 2: no fluorescence and very little reflection visible, sample appears dark
Comparative Example 3: visible orange fluorescence
Measurements

TABLE 5

| Sample | L* | a* | b* | Rel. fluorescence intensity [%] | Fluorescence maximum [nm] |
|---|---|---|---|---|---|
| Ref. Sample 1 | 85.50 | 0.26 | 7.56 | 100 | 440 (blue) |
| Ref. Sample 2 | 86.86 | −1.09 | 3.90 | 8 | none |
| Inv. Example 1 | 81.82 | 0.39 | 33.55 | 38 | 450 (blue) |
| Inv. Example 2 | 81.17 | 1.81 | 32.42 | 37 | 500 (blue/green) 610 (orange/red) |
| Comp. Example 1 | 84.55 | −1.36 | 14.01 | 5 | None |
| Comp. Example 2 | 78.81 | 1.84 | 39.17 | 0 | none |
| Comp. Example 3 | 79.54 | 1.34 | 44.08 | −30** | 610 (orange/red) |

**Due to the undesired orange fluorescence of the praseodymium ions and the lack of desired fluorescence of the bismuth ions, the defined "background area" between 550 nm and 710 nm shows a higher emission intensity than the defined "fluorescence area" between 410 nm and 540 nm. This leads to a negative value of the relative fluorescence intensity.

The metal ion concentrations in the sample solutions were calculated to be the same in the two Inventive Example solutions and in the Comparative Example solution (based on mol/l).

The fluorescence of the zirconia samples which were colored with the Tb or Pr ions containing solutions was clearly stronger than the fluorescence of the zirconia samples which were colored with the Fe ions containing solution. Hence, a more intense fluorescence could be retained (sometimes even while going to darker tooth colors, i.e. higher b* values) when using Tb or Pr as the yellow coloring agent.

The invention claimed is:

1. A solution for coloring and imparting fluorescence to a zirconia dental article, the solution comprising:
a solvent;
a coloring agent comprising metal ions selected from Tb, Er, Pr, Mn and combinations thereof;
a fluorescing agent comprising ions of Bi; and
the solution not comprising Fe ions in an amount above about 0.05 wt.-% with respect to the weight of the solution.

2. The solution of claim 1, wherein the molar ratio of the ions of the fluorescing agent to the ions of the coloring agent is in a range from about 1:10 to about 1:2000.

3. The solution of claim 1, wherein the solvent is selected from water, alcohols, ketones, glycols and combinations thereof.

4. The solution of claim 1 further comprising:
complexing agent(s);
thickening agent(s);
marker substance(s);
additive(s);
or combinations thereof.

5. The solution of claim 1, wherein the solution has a pH value of 0 to 9, if the solution contains water; has a viscosity of 1 to 2,000 mPa*s at 23° C.; is transparent, or a combination thereof.

6. The solution of claim 1 further comprising the components in the following amounts:
solvent: from about 15 to about 99 wt.-% calculated with respect to the amount of the solution,
coloring agent comprising metal ions in an amount from about 0.05 to about 10 wt.-%, of metal ions in the coloring agent calculated with respect to the amount of the solution, and
fluorescing agent: from about 0.005 to about 3 wt.-%, calculated with respect to the amount of the solution.

7. The solution of claim 1, wherein the solution does not include ions selected from Dy, Nd, Sm, Eu and combinations thereof in an amount above about 0.1 wt.-% with respect to the weight of the solution, insoluble particles selected from SiO2, TiO2, ZrO2 and combinations thereof, or both.

8. The solution of claim 1 comprising:
   water as solvent in an amount of 20 to 95 wt.-% calculated with respect to the weight of the solution,
   coloring agent comprising ions of Tb, Er, Mn or combinations thereof in an amount of 0.2 to 8 wt.-% of the total Tb, Er and Mn ions, calculated with respect to the weight of the solution, and
   fluorescence agent comprising ions of Bi in an amount of 0.02 to 2 wt.-%, calculated with respect to the weight of the solution, and wherein
   the solution has a pH value in the range of 0 to 9;
   the solution has a viscosity in the range of 1 to 2,000 mPa*s at 23° C.;
   the solution does not include Fe ions in an amount above 0.05 wt.-%; and
   the solution does not include ions selected from Dy, Nd, Sm, Eu or combinations thereof in an amount above about 0.1 wt.-% calculated with respect to the weight of the solution.

9. A device comprising a reservoir and an opening, wherein the reservoir containing the solution as described in claim 1.

10. A process of coloring a zirconia dental article, the process comprising:
    providing a zirconia dental article, the zirconia dental article being porous;
    treating the zirconia dental article with the solution described in claim 1; and
    optionally heating the treated porous zirconia dental article until at least 99.5% of the theoretical density is achieved.

11. The process of claim 10, wherein the zirconia dental article has the shape of a crown, bridge, inlay, onlay, veneer, facing, coping, crown and bridged framework, implant, abutment, orthodontic appliances, or dental milling block and parts thereof.

12. The process of claim 11, wherein the zirconia dental article is prepared by heat treating a zirconia aerogel.

13. The process of claim 12, wherein the zirconia dental article is characterized by the following features:
    a) showing a N2 adsorption and desorption of type IV with a hysteresis loop of type H1 according to IUPAC classification in a p/p0 range of 0.70 to 0.95;
    b) average connected pore diameter: from about 10 to about 100 nm; and
    c) BET surface: from about 10 to about 200 $m^2/g$.

14. A kit of parts comprising:
    the solution of claim 1;
    a zirconia dental article, wherein the zirconia dental article is porous
    optionally application equipment, and
    optionally an instruction for use.

15. A kit of parts comprising; a receptacle containing a coloring liquid (A) and a receptacle containing a fluorescence liquid (B),
    wherein the coloring liquid (A) comprises a solvent and coloring agent comprising ions selected from Tb, Er, Pr, Mn and combinations thereof,
    wherein the fluorescing liquid (B) comprises a solvent and fluorescing agent comprising ions of Bi, and
    wherein the coloring liquid (A) and the fluorescing liquid (B), if mixed to form a mixture, does not comprise Fe ions in an amount above about 0.05 wt.-% with respect to the weight of the mixture.

* * * * *

UNITED STATES PATENT AND TRADEMARK OFFICE
CERTIFICATE OF CORRECTION

PATENT NO. : 9,757,310 B2
APPLICATION NO. : 14/774485
DATED : September 12, 2017
INVENTOR(S) : Michael Jahns It is certified that error appears in the above-identified patent and that said Letters Patent is hereby corrected as shown below:

On the Title Page

Column 2
(Other Publications), Line 8, delete "Charactgerization" and insert -- Characterization --, therefor.

Column 2
(Other Publications), Page 2, Line 48, delete "Microstructur4e," and insert -- Microstructure, --, therefor.

Column 2
(Other Publications), Page 2, Line 48, delete "Flecural" and insert -- Flexural --, therefor.

In the Specification

Column 11
Line 55, delete "ketons." and insert -- ketones. --, therefor.

Column 12
Line 32, delete "gluturate," and insert -- glutarate, --, therefor.

Column 12
Lines 63-64, delete "triethylentetramine," and insert --triethylenetetramine, --, therefor.

Column 12
Line 65, delete "phthalocyanin," and insert -- phthalocyanine, --, therefor.

Column 13
Line 5, delete "ethylendiamin" and insert -- ethylenediamine --, therefor.

Signed and Sealed this
Eighth Day of May, 2018

Andrei Iancu
*Director of the United States Patent and Trademark Office*

Column 13
Lines 66-67, delete "hydrochinone," and insert -- hydroquinone, --, therefor.

Column 14
Line 28 (approx.), delete "limit" and insert -- limit: --, therefor.

Column 14
Line 55, delete "limit" and insert -- limit: --, therefor.

Column 14
Line 64 (approx.), delete "limit" and insert -- limit: --, therefor.

Column 15
Line 5 (approx.), delete "limit" and insert -- limit: --, therefor.

Column 17
Line 46, delete "article," and insert -- article. --, therefor.

Column 17
Line 64, delete "Rhodamin" and insert -- Rhodamine --, therefor.

Column 17
Line 65, delete "0=about" and insert -- Ø=about --, therefor.

Column 19
Line 58, delete "sprectrometry" and insert -- spectrometry --, therefor.

Column 20
Line 5 (approx.), delete "exitation" and insert -- excitation --, therefor.

Column 22
Line 32 (approx.), delete ""AMBERLYTE" and insert -- "AMBERLITE --, therefor.

Column 22
Line 37, (approx.), delete "Lathanum" and insert -- Lanthanum --, therefor.